(12) United States Patent
Doi

(10) Patent No.: US 6,446,645 B1
(45) Date of Patent: Sep. 10, 2002

(54) DIP CLEANING SYSTEM FOR A SUBSTRATE, SYSTEM FOR EVALUATING THE AMOUNT OF PARTICLES AND METHOD OF EVALUATING THE AMOUNT OF PARTICLES ADHERING TO A SUBSTRATE

(75) Inventor: Minoru Doi, Kanagawa (JP)

(73) Assignee: Semiconductor Leading Edge Technologies, Inc., Kanagawa (JP)

( * ) Notice: Subject to any disclaimer, the term of this patent is extended or adjusted under 35 U.S.C. 154(b) by 0 days.

(21) Appl. No.: 09/584,752

(22) Filed: Jun. 1, 2000

(30) Foreign Application Priority Data

Jun. 3, 1999 (JP) .......................................... 11-156608

(51) Int. Cl.$^7$ ................................................ B08B 3/00
(52) U.S. Cl. ...................... 134/61; 134/94.1; 134/113; 134/902
(58) Field of Search ........................ 134/18, 902, 56 R, 134/57 R, 58 R, 61, 94.1, 113

(56) References Cited

U.S. PATENT DOCUMENTS

| | | | | |
|---|---|---|---|---|
| 4,778,532 A | * | 10/1988 | McConnell et al. | 134/10 |
| 5,511,569 A | * | 4/1996 | Mukogawa | 134/104.1 |
| 5,722,441 A | * | 3/1998 | Teramoto | 134/113 |
| 6,241,827 B1 | * | 6/2001 | Tanaka et al. | 134/10 |

FOREIGN PATENT DOCUMENTS

| | | | | |
|---|---|---|---|---|
| JP | 01-231329 | * | 9/1989 | 34/218 |
| JP | 07-283190 | * | 10/1995 | 34/218 |

* cited by examiner

*Primary Examiner*—Randy Gulakowski
*Assistant Examiner*—Joseph L Perrin
(74) *Attorney, Agent, or Firm*—Foley & Lardner

(57) ABSTRACT

There are provided an system for evaluating the amount of particles, a dip cleaning system, and a method of evaluating the amount of particles adhering to a substrate, which enable high-precision quantitative evaluation of the amount of particles suspended in a liquid without use of a monitor substrate, which enable easy determination of the correlation between the amount of particles suspended in the liquid and the amount of particles adhering to the substrate which is an object of cleaning, and which enable low-cost and highly-reliable cleaning evaluation. A residual liquid recovery pan for recovering a residual liquid interposed and a residual liquid quantitative measurement bath for measuring the amount of submerged particles is interposed, between the first substrate treatment bath and the second substrate treatment bath. A sample liquid is prepared by recovering a residual liquid dropped from the substrate by the residual liquid recovery pan and the residual liquid quantitative measurement bath when the substrate is transported from the first substrate treatment bath to the second substrate treatment bath through use of the substrate transportation structure. The sample liquid stored in the pure water metering bath is diluted with a predetermined amount of pure water by means of supplying pure water from the pure water supply source to the pure water metering bath. The amount of particles suspended in the thus-diluted sample liquid is measured through use of the submerged particle counter.

10 Claims, 1 Drawing Sheet

DIP CLEANING SYSTEM FOR A SUBSTRATE, SYSTEM FOR EVALUATING THE AMOUNT OF PARTICLES AND METHOD OF EVALUATING THE AMOUNT OF PARTICLES ADHERING TO A SUBSTRATE

BACKGROUND OF THE INVENTION

1. Field of the Invention

The present invention relates to the technique of evaluating the cleanliness of a substrate to be used for an electronic device and a cleaning technique, and more particularly, to a system for evaluating the amount of particles, a dip cleaning system, and a method of evaluating the amount of particles adhering to a substrate (hereinafter referred to simply as a "particle quantity evaluation method"), which enable high-precision quantitative evaluation of the amount of particles, i.e. the amount of dust particles, suspended in a liquid without use of a monitor substrate, which enable easy determination of the correlation between the amount of particles suspended in the liquid and the amount of particles adhering to the substrate which is an object of cleaning.

2. Background Art

Recent explosive proliferation of mobile communications equipment or multimedia equipment necessitates urgent measures to reduce a line width of a system LSI, a liquid crystal device, or a like device to be housed in such equipment, and to curtail device cost. Against such a technical backdrop, development of a low-cost technique for cleaning a substrate to be employed in a system LSI (a large-scale integrated circuit), a liquid crystal device, or a like device is indispensable. A dip cleaning system has been widely used for satisfying these requirements.

A dip cleaning system, for cleaning a substrate employed in an LSI, a liquid crystal device, or a like device, evaluates, in the course of a dip cleaning operation, the amount of particles, i.e. dust particles, originating from an apparatus, a chemical, or purified water, and evaluates the amount of particles adhering to a substrate which is an object of cleaning. The amount of dust originating from an apparatus or a substrate is usually evaluated on the basis of the amount of dust particle determined through cleaning of a monitor substrate. The number of particles suspended in a dip chemical treatment bath and the number of those suspended in a rinsing bath are evaluated by means of the technique of evaluating the amount of particles (background art of a first type), in which are directly sampled from a substrate treatment bath, i.e., a chemical treatment bath or rinsing bath.

Further, there has already been disclosed another technique for evaluating the amount of particles, in which, for example, the amount of particles suspended in a liquid stored in a chemical treatment bath is measured, to thereby evaluate the state of dust particle (background art of a second type).

There has also been disclosed still another technique for evaluating the amount of particles, in which, for example, the amount of particles suspended in a rinsing bath is measured (background art of a third type).

Background art of the first type suffers the following three problems: cost of a monitor substrate (a first problem); deterioration of productivity caused by treatment of a monitor substrate (a second problem); and comparatively unreliable evaluation, because the state of the surface of a monitor substrate differs from that of the surface of a substrate to be cleaned and the condition of particle adhesion differs according to the type of dust particles (a third problem).

Background art of the second type suffers the following three problems. A submerged-particle counter meets difficulty in returning to its initial state in a case where a large amount of dust particles have originated from a substrate to be cleaned (a first problem). A submerged-particle counter erroneously counts as particle bubbles of hydrogen peroxide ($H_2O_2$) which develop when a large amount of liquid hydrogen peroxide is present in a chemical (a second problem). Further, detection sensitivity is low in the case of a chemical of high concentration or at high temperature (a third problem).

Background art of the third type suffers the following two problems.

It is difficult to count the number of particles, because dust particles disperse immediately after a substrate is immersed in a rinsing bath, thus resulting in an extreme reduction in particle count (a first problem). A large measurement error stems from a difference in particle counts, because a stream present in a water cleaning bath is apt to change according to a flow rate of water supplied to the rinsing bath or the viscosity of a chemical used for treatment.

SUMMARY OF THE INVENTION

The present invention has been conceived in view of the previously-described drawbacks of the background art and is aimed at providing an system for evaluating the amount of particles, a dip cleaning system, and a method of evaluating the amount of particles adhering to a substrate, which enable high-precision quantitative evaluation of the amount of dust particles suspended in a liquid without use of a monitor substrate, which enable easy determination of the correlation between the amount of particles suspended in the liquid and the amount of particles adhering to the substrate which is an object of cleaning, and which enable low-cost and highly-reliable cleaning evaluation.

According to one aspect of the present invention, a system for evaluating the amount of particles adhering to a substrate is provided. The system comprises a residual liquid recovery pan for recovering a drop of residual liquid falling from the surface of the substrate. A pure water metering bath is provided for use in measuring particles suspended in pure water, as well as for effecting a standby state in which the bath is filled with a predetermined amount of pure water. A pure water supply source is provided for supplying pure water to the pure water metering bath. A residual liquid quantitative measurement bath is provided which drips a predetermined amount of sample liquid supplied from the residual liquid recovery pan into the pure water stored in the pure water metering bath. Further, a submerged-particle counter is provided for evaluating submerged particles and counting the number of submerged particles, through use of the solution which has been obtained by means of dropping a drop of sample liquid of given amount into pure water.

According to another aspect of the present invention, a dip cleaning system for evaluating the amount of particles adhering to a substrate is provided. The system comprises a first substrate treatment bath having a chemical treatment bath and/or a rinsing bath for dip cleaning purpose. Also provided is a second substrate treatment bath having a chemical treatment bath and/or a rinsing bath for dip cleaning purpose. Substrate transport means is provided for transporting the substrate from the first substrate treatment bath to the second substrate treatment bath. Further, a sub-system for evaluating the amount of particles adhering to the substrate as defined above is provided.

According to another aspect of the present invention, a method of evaluating an amount of particles adhering to a substrate includes the following steps. In a first and a second substrate steps, a substrate is chemical treated and/or a rinsed for dip cleaning purpose. In a substrate transportation step, the substrate is transported from the first substrate step to the second substrate step. In a residual liquid recovery step, a sample liquid is prepared by means of recovering a residual liquid dropping from the surface of the substrate during the course of the substrate being transported from the first substrate step to the second substrate step. In a pure water metering step, the bath is filled with a predetermined amount of pure water for effecting a measurement of the amount of particles suspended in pure water, as well as effecting a standby state. In a pure water supply step, pure water is supplied to the pure water metering step. In a residual liquid quantitative measurement step, the sample liquid of given amount determined by the residual liquid recovery step is dropped into the pure water prepared by the pure water metering step, and the measurement of the amount of particles adhering to a substrate is performed.

Other features and advantages of the invention will be apparent from the following description taken in connection with the accompanying drawings.

DETAILED DESCRIPTION OF THE PREFERRED EMBODIMENT

Figure 1:
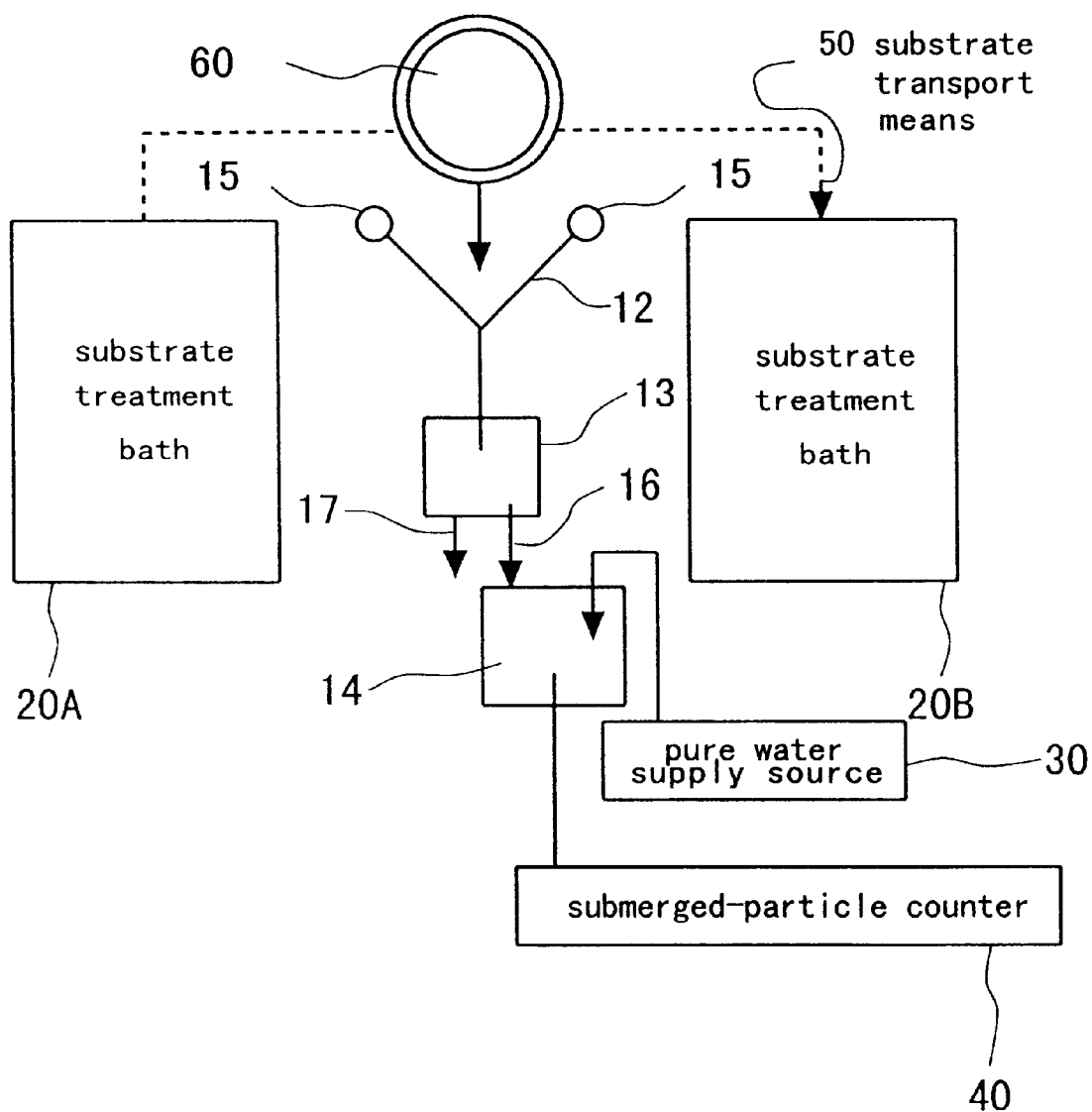
FIG. 1 shows a schematic system configuration of a dip cleaning system for a substrate according to an embodiment of the present invention, which includes a sub-system for evaluating the amount of particles adhering to a substrate, such as a semiconductor substrate.

A preferred embodiment of the present invention, which will be described hereinbelow, is directed to a dip cleaning system for cleaning a substrate with a chemical or a pure water, to thereby provide a clean substrate required for manufacture of a large-scale integrated circuit (LSI), a liquid crystal device, or a like device. The substrate is made free of particles (dust particles), metal impurities, or minute contaminants, such as organic substances.

The present embodiment is characterized in that measuring the cleanliness of a substrate can be effected in the form of measuring the amount of submerged particles after the substrate has been subjected to chemical treatment or water rinsing, by recovering a residual liquid remaining on the surface of a substrate after the substrate has been subjected to chemical treatment or water cleaning, through use of a residual liquid recovery pan and a residual liquid quantitative measurement bath, to thereby produce a sample liquid. A given amount of sample liquid is introduced into a metered amount of pure water which is stored in a pure water metering bath and whose initial values have already been measured, to thereby measure the number of particles suspended in the liquid, i.e., quantitative evaluation of the amount of particles.

The embodiments will be described hereinbelow in detail by reference to the accompanying drawings.

The term "pure water" is a relative term and is intended to mean water of a purity necessary to carry out a given process for a given class of devices. Accordingly, the purity will vary depending on the class of devices being processed.

By way of example, for 16M class memory devices pure water comprises water that includes less than 0.5 particles per cc of particles larger than 0.06 $\mu$M diameter. For 4M class memory devices, pure water comprises less than 1 particle per cc of particles larger than 0.08 $\mu$M in diameter.

FIG. 1 is a schematic system configuration diagram for describing a dip cleaning system of a substrate according to an embodiment of the present invention. The dip cleaning system includes a sub-system for evaluating the amount of particles adhering to a substrate, such as a semiconductor substrate.

In FIG. 1, reference numeral 12 designates a residual liquid recovery pan; 13 designates a residual liquid quantitative measurement bath; 14 designates a pure water metering bath; 15 designates a pure water nozzle; 16 designates a pure water pipe; 17 designates a waste fluid pipe; 20A designates a first substrate treatment bath; 20B designates a second substrate treatment bath; 30 designates a pure water supply source; 40 designates a submerged-particle counter; 50 designates substrate transport means; and 60 designates a substrate which is an object of cleaning.

The dip cleaning system of the present embodiment enables high-precision quantitative evaluation of the amount of particles which are actually suspended in a liquid, without involvement of use of a monitor substrate. Further, the dip cleaning system enables easy determination of the correlation between the amount of particles suspended in a liquid and the amount of particles adhering to the substrate 60 which is an object of dip cleaning, thus enabling low-cost and highly-reliable evaluation of cleanliness of the substrate 60.

The dip cleaning system comprises the first substrate treatment bath 20A and the second substrate treatment bath 20B, the substrate transport means 50, and a sub-system for evaluating the amount of particles (hereinafter referred to simply as a "particle quantity evaluation system") which will be described later.

The first substrate treatment bath 20A has a chemical treatment bath and/or a rinsing bath for dip cleaning purpose, and the second substrate treatment bath 20B has a chemical treatment bath and/or a rinsing bath for dip cleaning purpose. The substrate transport means 50 transports the substrate 60 from the first substrate treatment bath 20A to the second substrate treatment bath 20B.

The particle quantity evaluation system of the present embodiment enables high-precision quantitative evaluation of the amount of particles which are actually suspended in a liquid, without involvement of use of a monitor substrate. Further, the particle quantity evaluation system enables easy determination of the correlation between the amount of particles suspended in a liquid and the amount of particles adhering to the substrate, thus enabling low-cost, highly-reliable valuation of cleanliness of the substrate 60.

The particle quantity evaluation system comprises the residual liquid recovery pan 12, the residual liquid quantitative measurement bath 13, the pure water metering bath 14, the pure water nozzle 15, the pure water pipe 16, the waste fluid pipe 17, the pure water supply source 30, and the submerged-particle counter 40.

The residual liquid recovery pan 12 recovers at least a drop of residual liquid falling from the surface of the substrate 60 when the substrate 60 is transported from the first substrate treatment bath 20A to the second substrate treatment bath 20B, thus preparing a sample liquid. A sample liquid to be diluted is quantitatively measured, to thereby count the number of particles for evaluation.

Therefore, the correlation between the amount of particles suspended in the liquid and the amount of dust particles adhering to the substrate 60 is determined easily, thereby greatly improving the accuracy of the correlation. The pure water metering bath 14 is a rinsing bath for use in measuring particles suspended in pure water and is in a standby state in which the bath is filled with a predetermined amount of pure water.

The pure water supply source 30 supplies pure water to the pure water metering bath 14 while remaining in communication with the pure water metering bath 14. Before measurement of a sample liquid, pure water is circulated to the submerged-particle counter 40, thus maintaining the initial state of the submerged-particle counter 40. The number of particles is counted for evaluation after pure water to be used for dilution and the sample liquid have been metered, thus facilitating determination of the correlation between the amount of particles suspended in the sample liquid and the amount of dust particles adhering to the substrate 60. Further, the accuracy of the correlation is improved.

The residual liquid quantitative measurement bath 13 drips a predetermined amount of sample liquid supplied from the residual liquid recovery pan 12 into the pure water stored in the pure water metering bath 14, while remaining in communication with the residual liquid recovery pan 12 located at an upstream position and with the pure water metering bath 14 located at a downstream position via the pure water pipe 16. A prescribed amount of liquid is dropped from the residual liquid quantitative measurement bath 13 into the pure water metering bath 14 retaining a predetermined amount of water as a reference. Accordingly, the amount of particles suspended in the sample liquid can be quantitatively evaluated while measurement errors, which would otherwise be caused by a reduction in the amount of dust particles adhering to the substrate or occurrence of air bubbles, are avoided.

The submerged-particle counter 40 evaluates submerged particles and counts the number of submerged particles, through use of the solution which has been obtained by means of dropping at least a drop of sample liquid of given amount into pure water. In this way, a residual liquid remaining on the surface of the substrate 60 which has been cleaned in the first substrate treatment bath 20A is used for evaluation, thereby enabling highly-reliable measurement of cleanliness of the substrate 60 in the form of the amount of submerged particle. The measurement may be performed even after the substrate 60 has been subjected to chemical treatment.

The pure water nozzle 15 rinses the residual liquid recovery pan 12 and/or the residual liquid quantitative measurement bath 13, and the waste fluid pipe 17 drains the water used for rinsing the residual liquid recovery pan 12 and/or the residual liquid quantitative measurement bath 13.

As described above, the particle quantity evaluation system is equipped with a residual liquid recovery pan 12 for recovering a residual liquid interposed between the first substrate treatment bath 20A and the second substrate treatment bath 20B, and the residual liquid quantitative measurement bath 13 for measuring the amount of submerged particles. When the substrate 60 is transported from the first substrate treatment bath 20A to the second substrate treatment bath 20B through use of the substrate transportation means 50, a residual liquid dropped from the substrate 60 is collected by the residual liquid recovery pan 12 and the residual liquid quantitative measurement bath 13, where a sample liquid is produced. Pure water is supplied from the pure water supply source 30 to the pure water metering bath 14, to thereby dilute the sample liquid stored in the pure water metering bath 14 with a predetermined amount of pure water. The amount of particles suspended in the thus-diluted sample liquid is measured by the submerged particle counter 40.

The operation of the dip cleaning system and the particle quantity evaluation method will now be described. The dip cleaning system of the present embodiment enables high-precision quantitative evaluation of the amount of particles actually suspended in a liquid without use of a monitor substrate. The dip cleaning system enables easy determination of the correlation between the amount of particles suspended in the liquid and the amount of particles adhering to the substrate 60 which is an object of dip cleaning. The dip cleaning system enables a low-cost and highly-reliable evaluation of cleaning.

The dip cleaning system performs the particle quantity evaluation method comprising a first substrate step, a second substrate step, a substrate transportation step, a residual liquid recovery step, a pure water metering step, a pure water supply step, a residual water quantitative measurement step, and a submerged particle measurement step. Each step will be described below.

Processing pertaining to the first substrate step is to be performed by the first substrate treatment bath 20A, and the first substrate step has a chemical step for dip cleaning purpose and/or a rinsing step. Processing pertaining to the second substrate step is to be performed by the second substrate treatment bath 20B, and the second substrate step has a chemical step for dip cleaning purpose and/or a rinsing step. Processing pertaining to the substrate transportation step is to be performed by the substrate transportation means 50. In the transportation step, the substrate 60 is transported from the first substrate step to the second substrate step. Processing pertaining to the residual liquid recovery step is to be performed by the residual liquid recovery pan 12. During the course of the substrate 60 being transported from the first substrate step to the second substrate step, a residual liquid dropping from the surface of the substrate 60 is collected, to thereby produce a sample liquid. Processing pertaining to the pure water metering step is to be performed by the pure water metering bath 14. In this step, in order to perform measurement of particles suspended in pure water, and there is effected a standby state in which the bath is filled with a predetermined amount of pure water. Processing pertaining to the pure water supply step is to be effected by the pure water supply source 30, and pure water is supplied to the pure water metering step. Processing pertaining to the residual liquid quantitative measurement step is to be effected by the residual liquid quantitative measurement bath 13. In this step, the sample liquid of given amount determined by the residual liquid recovery step is dropped into the pure water which is to be used in the pure water metering step. Processing pertaining to the submerged particle measurement step is to be performed by the submerged particle counter 40. The number of submerged particles is counted for evaluation through use of the solution prepared by means of dropping a sample liquid of given amount into pure water. Further, in the pure water supply step, before measurement of a sample liquid, pure water is circulated to the submerged-particle counter 40, thus maintaining the initial state of the submerged-particle counter 40.

In the particle quantity evaluation system and method having the above-described configuration, the residual liquid recovery step is performed for recovering a residual liquid and to the residual liquid quantitative measurement step is performed for measuring the amount of submerged particles, and the steps are interposed between the first substrate step and the second substrate step. The residual liquid recovery step is performed when the substrate 60 is transported to the second substrate step after having been subjected to processing in the first substrate step. Residual liquid dropped from the substrate 60 is collected in the residual liquid recovery step and a sample liquid is produced in the residual liquid quantitative measurement step. The submerged particle measurement step is performed in which the sample liquid is diluted with a predetermined amount of pure water by means of supplying pure water from the pure water supply step to the pure water metering step, and the amount of particles suspended in the thus-diluted sample liquid is measured.

More specifically, the substrate 60 is subjected to treatment in the first substrate treatment bath 20A. When the substrate 60A is transported to the second substrate treatment bath 20B, a drop or drops of residual liquid is collected by the residual liquid recovery pan 12 and the residual liquid quantitative measurement bath 13, where a sample liquid is prepared. The thus-prepared sample liquid is subjected to quantitative measurement in the residual liquid quantitative measurement bath 13. During quantitative measurement being performed, the pure water metering bath 14 effects a standby state in which the bath is filled with a predetermined amount of pure water, in preparation for particle measurement. After the pure water metering path 14 having entered a standby state, the pure water pipe 16 remaining in communication with the pure water metering bath 14 is opened to introduce a sample liquid of given amount, and the amount of submerged particles is measured by the submerged particle counter 40. Subsequently, the residual liquid recovery pan 12 and the residual liquid quantitative measurement bath 13 are cleaned through use of the pure water nozzle 15, 50 that recovery of the next residual liquid is ready to be performed. Pure water used for cleaning is drained by way of the waste fluid pipe 17 which is to be used when the pure water nozzle 15 performs a cleaning operation. A model corresponding to one set is illustrated for indicating the flow of processing pertaining to round of steps. In a case where treatment of the substrate 60 requires a short period of tact time, a plurality of sets must be employed.

As has been described, the embodiment of the present invention yields the following advantages. Highly-sensitive, low-cost, and highly-reliable evaluation of cleanliness can be effected on a per-substrate-lot basis (a first advantage). The amount of residual particles adhering to the substrate 60 can be grasped, which in turn enables taking of measures for reducing the amount of dust particles and improving yield (a second advantage). The embodiment of the present invention may be applied to the dip cleaning method for removing particles adhering to the substrate 60, which would be primarily responsible for a drop in the manufacturing yield of an LSI device or a liquid crystal device. Thus, the amount of dust particles adhering to the substrate 60 can be diminished, thus enabling a reduction in manufacturing cost and attainment of stable productivity.

The present invention is not limited to the preceding embodiment, and it is readily apparent that the embodiment of the invention is susceptible to various modifications, as necessary, within the scope of the invention. The number, positions, and shapes of the constituent elements are not limited to those described in the embodiment, and may be changed to those desirable for carrying out the invention.

The present invention is embodied in the manner as mentioned previously, and the effects and the advantages may be summarized as follows.

Namely, highly-sensitive, low-cost, and highly-reliable evaluation of cleanliness can be effected on a per-substrate-lot basis (a first advantage). The amount of residual particles adhering to the substrate 60 can be grasped, which in turn enables taking of measures for reducing the amount of dust particles and improving yield (a second advantage). The present invention may be applied to a dip cleaning method for removing particles adhering to the substrate 60, and the amount of dust particles adhering to the substrate 60 can be diminished, thus enabling a reduction in manufacturing cost and attainment of stable productivity.

It is further understood that the foregoing description is a preferred embodiment of the disclosed system and method and that various changes and modifications may be made in the invention without departing from the spirit and scope thereof.

The entire disclosure of a Japanese Patent Application No. 11-156608, filed on Jun. 3, 1999 including specification, claims, drawings and summary, on which the Convention priority of the present application is based, are incorporated herein by reference in its entirety.

I claim:

1. A system for evaluating the amount of particles adhering to a substrate, the system comprising:

a residual liquid recovery pan for recovering residual liquid falling from a surface of a substrate when the substrate is transported from a first substrate treatment bath to a second substrate treatment bath, thus forming a sample liquid;

a pure water metering bath for measuring particles suspended in a predetermined amount of pure water;

a pure water supply source for supplying the predetermined amount of pure water to the pure water metering bath;

a residual liquid quantitative measurement bath which supplies a predetermined amount of the sample liquid supplied from the residual liquid recovery pan into the predetermined amount of pure water in the pure water metering bath; and a submerged-particle counter for evaluating submerged particles and counting a number of submerged particles in a mixture of the predetermined amount of sample liquid and the predetermined amount of pure water in the pure water metering bath.

2. The system for evaluating the amount of particles as defined in claim 1, wherein the pure water supply source is configured so as to maintain an initial state of the pure water metering bath before measurement of a sample liquid by circulation of pure water to the pure water metering bath.

3. The system for evaluating the amount of particles as defined in claim 1, further comprising a pure water rinsing nozzle for rinsing the residual liquid recovery pan, and the residual liquid quantitative measurement bath.

4. The system for evaluating the amount of particles as defined in claim 1, further comprising a pure water nozzle for rinsing at least one of the residual liquid recovery pan, the residual liquid quantitative measurement bath, a waste fluid pipe for draining the water used for rinsing the residual liquid recovery pan, and the residual liquid quantitative measurement bath.

5. A dip cleaning system for evaluating the amount of particles adhering to a substrate, the system comprising:

a first substrate treatment bath for treating the substrate;

a second substrate treatment bath for treating the substrate;

substrate transportation structure for transporting the substrate from the first substrate treatment bath to the second substrate treatment bath; and a sub-system for evaluating the amount of particles adhering to a substrate, the sub-system including:

a residual liquid recovery pan for recovering residual liquid falling from the surface of the substrate when the substrate is transported from the first substrate treatment bath to the second substrate treatment bath, and forming a sample liquid from the recovered residual liquid;

a pure water metering bath for measuring particles suspended in pure water;

a pure water supply source for supplying pure water to the pure water metering bath;

a residual liquid quantitative measurement bath which supplies a predetermined amount of sample liquid from the residual liquid recovery pan into the pure water in the pure water metering bath; and a submerged-particle counter for evaluating and counting submerged particles in the pure water metering bath.

6. The dip cleaning system as defined in claim 5, further comprising:

a pure water rinsing structure comprising:

a pure water nozzle for rinsing at least one of the residual liquid recovery pan, the residual liquid quantitative measurement bath, a waste fluid pipe for draining the water used for rinsing the residual liquid recovery pan and the residual liquid quantitative measurement bath.

7. A dip cleaning system as defined in claim 5, wherein the first substrate treatment bath is a chemical treatment bath.

8. A dip cleaning system as defined in claim 5, wherein the first substrate treatment bath is a rinsing bath.

9. A dip cleaning system as defined in claim 5, wherein the second substrate treatment bath is a chemical treatment bath.

10. A dip cleaning system as defined in claim 5, wherein the second substrate treatment bath is a rinsing bath.

* * * * *